US010987052B2

(12) United States Patent
Macia Barber et al.

(10) Patent No.: US 10,987,052 B2
(45) Date of Patent: *Apr. 27, 2021

(54) SENSOR FOR ACQUIRING PHYSIOLOGICAL SIGNALS

(71) Applicant: Smart Solutions Technologies, S.L., Madrid (ES)

(72) Inventors: Agustin Macia Barber, Torrelodones (ES); Daniel Llorca Juan, Porto San Giorgio (IT)

(73) Assignee: Smart Solutions Technologies, S.L., Madrid (ES)

( * ) Notice: Subject to any disclaimer, the term of this patent is extended or adjusted under 35 U.S.C. 154(b) by 1078 days.

This patent is subject to a terminal disclaimer.

(21) Appl. No.: 15/461,275

(22) Filed: Mar. 16, 2017

(65) Prior Publication Data

US 2017/0188949 A1 Jul. 6, 2017

Related U.S. Application Data

(63) Continuation of application No. 13/988,007, filed as application No. PCT/EP2011/070296 on Nov. 16, 2011, now Pat. No. 9,629,584.

(Continued)

(30) Foreign Application Priority Data

Nov. 17, 2010 (EP) .................................... 10191590

(51) Int. Cl.
*A61B 5/00* (2006.01)
*A61B 5/0408* (2006.01)
(Continued)

(52) U.S. Cl.
CPC .......... *A61B 5/6804* (2013.01); *A61B 5/0205* (2013.01); *A61B 5/04085* (2013.01);
(Continued)

(58) Field of Classification Search
CPC . A61B 5/6804; A61B 5/0205; A61B 5/04085; A61B 5/0492; A61B 5/0245;
(Continued)

(56) References Cited

U.S. PATENT DOCUMENTS 3,954,100 A 5/1976 Sem-Jacobsen
3,993,049 A 11/1976 Kater
(Continued)

FOREIGN PATENT DOCUMENTS

CN 1732029 A 2/2006
EP 0788811 A1 8/1997
(Continued)

OTHER PUBLICATIONS

Carpi et al. "Electroactive Polymer-Based Devices for e-Textiles in Biomedicine" IEEE Transactions on Information Technology in Biomedicine 9(3): 295-318 (2005).
(Continued)

*Primary Examiner* — Eun Hwa Kim
*Assistant Examiner* — Adam Z Minchella
(74) *Attorney, Agent, or Firm* — Entralta P.C.; Justin G. Sanders; Peter D. Weinstein

(57) ABSTRACT

A device for acquiring and collecting physiological signals is disclosed. In at least one embodiment, the device provides an at least one sensor having a conductive layer comprising a conductive fabric of interlaced conductive and non-conductive fibers and a plurality of orifices throughout the conductive fabric, wherein the plurality of orifices are filled with a silicone rubber, and wherein the silicone rubber is attached to the conductive fabric without the use of an adhesive. An electrical connector is connected to the conductive layer, the electrical connector providing a separable interface between the conductive layer and an electronic instrument. The device further provides an electronic instru- (Continued)

ment for receiving and collecting signals acquired from the at least one sensor.

17 Claims, 12 Drawing Sheets

Related U.S. Application Data

(60) Provisional application No. 61/427,864, filed on Dec. 29, 2010.

(51) Int. Cl.
| | | |
|---|---|---|
| *A61B 5/0205* | (2006.01) | |
| *A61B 5/0492* | (2006.01) | |
| *A61B 5/0245* | (2006.01) | |
| *A61B 5/0531* | (2021.01) | |
| *A61B 5/08* | (2006.01) | |

(52) U.S. Cl.
CPC .......... *A61B 5/0492* (2013.01); *A61B 5/0245* (2013.01); *A61B 5/0531* (2013.01); *A61B 5/0816* (2013.01); *A61B 2562/125* (2013.01)

(58) Field of Classification Search
CPC ................. A61B 5/0531; A61B 5/0816; A61B 2562/125
See application file for complete search history.

(56) References Cited

U.S. PATENT DOCUMENTS

| | | | |
|---|---|---|---|
| 4,082,087 A | 4/1978 | Howson | |
| 4,664,118 A | 5/1987 | Batters | |
| 4,708,149 A | 11/1987 | Axelgaard et al. | |
| 4,867,166 A | 9/1989 | Axelgaard et al. | |
| 4,898,689 A | 2/1990 | Hamada et al. | |
| 4,941,961 A | 7/1990 | Noguchi et al. | |
| 5,164,443 A | 11/1992 | Watanabe | |
| 5,289,822 A | 3/1994 | Highe et al. | |
| 5,352,315 A | 10/1994 | Carrier et al. | |
| 5,427,096 A | 6/1995 | Bogusiewicz et al. | |
| 5,746,207 A | 5/1998 | McLaughlin et al. | |
| 5,947,897 A | 9/1999 | Otake | |
| 6,270,466 B1 | 8/2001 | Weinstein et al. | |
| 6,419,636 B1 | 7/2002 | Young et al. | |
| 6,745,082 B2 | 6/2004 | Axelgaard | |
| 7,173,437 B2 | 2/2007 | Hervieux et al. | |
| 7,324,841 B2 | 1/2008 | Reho et al. | |
| 7,502,643 B2 | 3/2009 | Farringdon et al. | |
| 7,522,951 B2 | 4/2009 | Gough et al. | |
| 7,779,656 B2 | 8/2010 | Dias et al. | |
| 7,783,334 B2 | 8/2010 | Nam et al. | |
| 8,112,140 B2 | 2/2012 | Grabetal | |
| 8,369,936 B2 | 2/2013 | Farringdon et al. | |
| 8,700,118 B2 | 4/2014 | Oster et al. | |
| 8,818,478 B2 | 8/2014 | Scheffler et al. | |
| 9,629,584 B2 * | 4/2017 | Macia Barber ...... | A61B 5/0205 |
| 2003/0163035 A1 | 8/2003 | Van Heerden et al. | |
| 2005/0177059 A1 | 8/2005 | Koivumaa et al. | |
| 2006/0094948 A1 | 5/2006 | Gough et al. | |
| 2006/0095001 A1 | 5/2006 | Matsumura et al. | |
| 2006/0183990 A1 * | 8/2006 | Tolvanen ............ | A61N 1/0484 600/386 |
| 2007/0060859 A1 | 3/2007 | Kanamura et al. | |
| 2007/0127187 A1 | 6/2007 | DeFusco et al. | |
| 2008/0242176 A1 | 10/2008 | Jaeger et al. | |
| 2008/0287769 A1 | 11/2008 | Kurzweil et al. | |
| 2009/0043185 A1 | 2/2009 | McAdams et al. | |
| 2009/0100566 A1 | 4/2009 | Schiavino et al. | |
| 2009/0282671 A1 | 11/2009 | Tao et al. | |
| 2010/0070007 A1 | 3/2010 | Parker et al. | |
| 2010/0185076 A1 | 7/2010 | Jeong et al. | |
| 2010/0198038 A1 | 8/2010 | Nagata et al. | |
| 2010/0198043 A1 | 8/2010 | Holzer et al. | |
| 2010/0234715 A1 | 9/2010 | Shin et al. | |
| 2011/0230749 A1 | 9/2011 | Chan et al. | |
| 2011/0259638 A1 | 10/2011 | Sherrill et al. | |
| 2012/0246795 A1 | 10/2012 | Scheffler et al. | |

FOREIGN PATENT DOCUMENTS

| | | |
|---|---|---|
| EP | 1361819 B1 | 11/2003 |
| EP | 2072009 A1 | 6/2009 |
| EP | 2196142 A1 | 6/2010 |
| JP | S55-108455 A | 8/1980 |
| JP | 2001-234070 A | 8/2001 |
| JP | 2006-512128 A | 4/2006 |
| JP | 2008-536542 A | 9/2008 |
| KR | 10-0863064 B1 | 10/2008 |
| RU | 2237303 C2 | 9/2004 |
| RU | 55241 u1 | 7/2006 |
| WO | 1997018450 A1 | 5/1997 |
| WO | 2001002052 A2 | 11/2001 |
| WO | 2002030279 A1 | 4/2002 |
| WO | 2002039894 A1 | 5/2002 |
| WO | 2002071935 A1 | 9/2002 |
| WO | 2004058346 A1 | 7/2004 |
| WO | 2004110192 A1 | 12/2004 |
| WO | 2005088772 A1 | 9/2005 |
| WO | 2006046703 A1 | 5/2006 |
| WO | 2006101748 A3 | 9/2006 |
| WO | 2007050650 A2 | 5/2007 |
| WO | 2009020274 A1 | 2/2009 |
| WO | 2009041496 A1 | 4/2009 |

OTHER PUBLICATIONS

De Rossi et al. "Wearable Technology for Biomechanics: e-Textile or Micromechanical Sensors?" IEEE Engineering in Medicine and Biology Magazine, 29: 37-43 (2010).
EPO Extended European Search Report, EP 10191590.8, dated Apr. 28, 2011.
EPO Extended European Search Report, EP 12174367.8, dated Oct. 1, 2012.
EPO Extended European Search Report, EP 16194210.7, dated Mar. 3, 2017.
Franta "Elastomers and Rubber Compounding Materials" Studies in Polymer Science 1, Elsevier, 1989, p. 241.
International Search Report and Written Opinion, PCT/EP2011/070296 dated Feb. 6, 2012.
International Search Report and Written Opinion, PCT/EP2012/056573 dated Sep. 28, 2012.
International Search Report, PCT/EP2013/063861, dated Sep. 20, 2013.
Polar WearLink® + Coded Transmitter 31 Coded Transmitter W.I.N.D. User Manual.
Saleem et al. "Fabrication of Extrinsically Conductive Silicone Rubbers with High Elasticity and Analysis of Their Mechanical and Electrical Characteristics" Polymers 2010, 2, 200-210; doi:10.3390/polym2030200 (2010).
The State Intellectual Property Office of the People's Republic of China Search Report, Application No. 201380044523X, dated Oct. 20, 2015, English Translation.

* cited by examiner

SENSOR FOR ACQUIRING PHYSIOLOGICAL SIGNALS

RELATED APPLICATIONS

This is a continuation application and so claims the benefit pursuant to 35 U.S.C. § 120 of a prior filed and co-pending U.S. non-provisional application Ser. No. 13/988,007 filed on May 16, 2013, which itself is a 35 U.S.C. § 371 U.S. national stage entry of international application serial number PCT/EP2011/070296, filed on Nov. 16, 2011, which claims priority to both U.S. provisional application Ser. No. 61/427,864, filed on Dec. 29, 2010, and EP application serial number 10191590.8, filed on Nov. 17, 2010. The contents of the aforementioned applications are incorporated by reference herein.

BACKGROUND

The present invention relates to sensors for acquiring physiological signals, devices comprising these sensors, as well as garments comprising these devices.

Applicant(s) hereby incorporate herein by reference any and all patents and published patent applications cited or referred to in this application.

By way of background, sensors comprising electrodes are used extensively in the assessment of clinical condition, for example in the monitoring of cardiac condition. The electrodes are placed in contact with the skin of the human body and the electrical physiological signals which result are examined.

Nevertheless, stability, noise and sensibility of the signals can be affected by different reasons; motion and long term acquisition of the signal are two of the most significant.

One of the physiological signals most affected by the different types of noise, as electrode contact noise or movement noise is the Electrocardiogram (ECG) signals. ECG is a long term analysis and to acquire a good signal it is crucial that the signal's parameters are stables.

As the ECG is a long term analysis, a garment that include an ECG sensor is essential to monitor this type of physiological signals in the daily live.

It is known in the state of the art, garments with sensors integrated in the textile. The sensor to be integrated in a garment must be a system minimal invasive, flexible, conformable to the human body including in movement, comfortable and resistant to repeated washing.

The current state of the art in textile sensors presents different drawbacks: i) Low adhesion to skin. Each relative motion between skin and electrode causes alterations in the signal. This limitation is very significant in the context of use of electrodes during physical activity. ii) Signal alterations. These are produced by the movement of the conductive fibers and the presence of wrinkles. iii) Decrease of the signal quality with time. In some sensors to ensure the skin contact, liquids such as water or grease can be used between the contact layer and the skin. In dry environments it is not possible to remain the skin moisture level constant and the electric conductivity of the contact layer decreases.

The patent application EP1361819, which applicant was Polar Electro, OY., describes a sensor which comprises a contact layer including conductive fibers, and a moisture layer for retaining moisture on the top of the contact layer. The moisture layer retains secretory products from the skin, such as moisture and electrolytes. This enhances the contact between the skin and the contact layer and increases the electric conductivity of the contact layer, but the confortable of the garment is minor as the humidity in the skin and inside the garment is increased.

The patent application EP2072009 describes a garment comprising at least one electrocardiogram sensor integrated into the garment comprising an electrode on the inside of the garment and arranged to contact a user's skin; and a resilient compressible filler provided between the garment and the electrode. The resilient compressible filler holds the electrode in place when the garment moves. The resilient compressible filler could be uncomfortable for the user.

The patent application US20100234715 describes a garment for measuring physiological signals. The garment including an electrode sensor coupled to an inner surface of a garment to make contact with the skin for detecting physiological signals; a signal connection line connected to the electrode sensor, a snap and a measurement unit. The electrode sensor unit is coupled to a desired portion of a garment using a coupling adhesive member which is may have opened frame shape for attaching edges of the electrode sensor to the garment. An anti slipping adhesive tape (member) may be formed along the border of the electrode sensor and the coupling adhesive member.

Thus, from what is known in the art, it is derived that the development of a sensor and a garment comprising the sensor which allow recording physiological signals, especially in movement, with improved adhesion properties but avoiding adhesive elements which produce skin irritations and with flexibility properties, is still of great interest.

Aspects of the present invention fulfill these needs and provide further related advantages as described in the following summary.

SUMMARY

Aspects of the present invention teach certain benefits in construction and use which give rise to the exemplary advantages described below.

The present invention solves the problems described above by providing a device for acquiring and collecting physiological signals. In at least one embodiment, the device provides an at least one sensor having a conductive layer comprising a conductive fabric of interlaced conductive and non-conductive fibers and a plurality of orifices throughout the conductive fabric, wherein the plurality of orifices are filled with a silicone rubber, and wherein the silicone rubber is attached to the conductive fabric without the use of an adhesive. An electrical connector is connected to the conductive layer, the electrical connector providing a separable interface between the conductive layer and an electronic instrument. The device further provides an electronic instrument for receiving and collecting signals acquired from the at least one sensor.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The accompanying drawings illustrate aspects of the present invention. In such drawings.

Figure 1A:
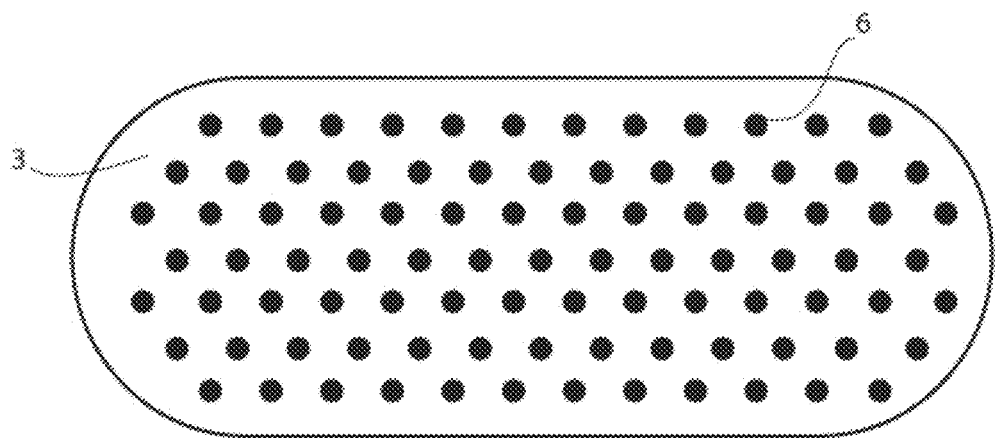
FIG. 1A illustrates an exemplary orifice pattern in an exemplary electrode, in accordance with at least one embodiment.

The above described drawing figures illustrate aspects of the invention in at least one of its exemplary embodiments, which are further defined in detail in the following description. Features, elements, and aspects of the invention that are referenced by the same numerals in different figures represent the same, equivalent, or similar features, elements, or aspects, in accordance with one or more embodiments.

DETAILED DESCRIPTION

A target of the present invention is the monitoring of the user in physical activity on a continuous and non-invasive mode, without adding any restrictions. Thus, the sensor 1 of the present invention allows measuring the electrical physiological signals during physical activity.

As mentioned above, a first aspect of the invention relates to a sensor 1 to be placed in contact with the skin 12 of an user for acquiring physiological signals which comprises: a) a conductive layer 2 comprising at least conductive fibers to be placed in contact with the skin 12 for receiving physiological signals; b) an electrical connector 5 connected to the conductive layer; characterized in that the conductive layer comprises a plurality of orifices 6 filled with an silicone rubber throughout the conductive area.

The term "sensor" as used herein, refers to a component that receives physiological signals and transforms them into electrical signals.

The term "electrode" as used herein, refers to the area of the conductive layer that is in contact with the skin and wherein the physiological signal is received.

The term "track" as used herein, refers to the area of the conductive layer where the electrical connector is located. The track transmitters the physiological signal from the electrode area to the electrical connector.

The term "electrical connector" as used herein, refers to an electromechanical device which provides a separable interface between two electronic subsystems, sensor and electronic instrument, without an unacceptable effect on signal integrity.

The term "anti-slip material" as used herein, refers to a material with a material/skin friction coefficient of al least 0.5. In a preferred embodiment, the anti-slip material is silicone rubber.

The term "hot melt adhesive" as used herein, refers to a thermoplastic, non-structural adhesive that flows when heated and hardens and strengthens as it cools.

The term "screen printing", as commonly known in the art, refers to a process made using a stencil in which image or design is print on a very fine mesh screen and the printable material is squeegeed onto the printing surface through the area of the screen that is not covered by the stencil.

Traditionally the process was called screen printing or silkscreen printing because silk was used in the process. Thus, "silk printing", "screen printing" and "silk screen printing" are synonymous among them.

In an embodiment of the first aspect of the invention, the conductive layer 2 is made of conductive material, selected from conductive fabric.

In another embodiment of the first aspect of the invention, it is provided a sensor 1 adapted to be integrated in a garment 7 so as to be placed in contact with skin 12 of a user during the use of the garment 7, wherein said sensor 1 comprises a conductive layer 2 to be placed in contact with the skin 12 for receiving physiological signals comprising at least: an electrode 3; a track 4; and an electrical connector 5 connected with the track 4; wherein the electrode 3 of the conductive layer 2 comprises a plurality of orifices 6 or grooves 11 in a predefined pattern filled with an anti-slip material. Preferably the electrode 3 of the conductive layer 2 comprises a plurality of orifices.

According to an embodiment of the invention the electrode 3 and the track 4 are made of the same or different material. In a preferred embodiment of the first aspect of the invention the electrode 3 and track 4 independently from each other is a conductive fabric comprising conductive fibers and non conductive fibers.

In a preferred embodiment of the first aspect of the invention, the electrode 3 and the track 4 refer to a conductive fabric made of conductive fibers.

In other preferred embodiment of the first aspect of the invention, the electrode 3 and track 4 refer to a conductive fabric made of conductive fibers and non conductive fibers.

Preferably, the conductive fibers are made of silver coated nylon (such as Xstatic® yarns from Laird Sauquoit Industries) and the non conductive fibers are made of nylon.

Non limiting examples of conductive fibers are fiber made of silver, copper, nickel, stainless steel, gold, non conductive fibers coated with a conductive material or mixtures thereof. Non limiting examples of coating conductive materials are silver, cooper, nickel, stainless stell, gold and silicone rubber loaded with carbon or silver powder.

Non limiting examples of non conductive fibers are wool, silk, cotton, flax, jute, acrylic fiber, polyamide polyester, nylon and/or with elastic yarns (such as LYCRA® branded spandex from Invista™ S.a.r.l).

The conductive layer with conductive and non conductive fibers are not only more flexible than the conductive layer formed from metal fibers only, but also tend to be lighter and more resistant to oxidation. Because the fibers can be knit tightly, the electrical conductivity of the fabric can be maintained despite a partial loss of the conductive coating on particular threads, whereas in metal fiber conductive fabrics, the fabric may lose operability after a break in one of the fibers, particularly if the fibers are spaced far apart. The amount of metal in the fabric is a compromise between the demand to increase the conductivity and the necessity to improve the touch sensation of the cloth.

As a result of the interlacing of fibers, the fabric shows a plurality of orifices 6 among fibers. According to an embodiment of the invention, the electrode is drilled or grooved in order to make additional orifices 6 or grooves 11 or to make larger the orifices 6 of the electrode in a predefined pattern.

The plurality of orifices 6 or grooves 11 present different pattern as circular, sinusoidal pattern, straight lines pattern, hexagon pattern and other different geometric shapes pattern, or a combination thereof. The plurality of orifices 6 form a matrix random or organized.

The presence of such orifices 6 or grooves 11 in the conductive layer results in an improvement of the elasticity of the layer. By filling the conductive layer orifices 6 or grooves 11 with the silicone rubber it is reached an improvement in the adherence of the sensor to the skin and at the same time it is improved the signal measured, because the noise of the signal is reduced.

The silicone rubber before the process of cured is in a liquid state. When the silicone is in the liquid state is printing in the fabric. This means that the union silicone-fabric is an union without an adhesive. The electrically conductive layer described in the invention is integrated into the fabric. The silicone in the liquid state when is printing in the fabric is capable to penetrate in the orifices of the fabric, anchoring with the structure of the conductive layer.

When the orifices 6 or grooves 11 are filled, the silicone rubber present a flat or relief profile. In a preferred embodiment the silicone rubber shows a relief profile.

In a preferred embodiment the silicone rubber is a silicone rubber with molecular weight comprised between 400 g/mol and 600 g/mol.

As described above the sensor 1 of the invention is to be placed in contact with the skin 12. In a preferred embodiment the proportion of conductive layer 2 to be in contact with the skin is comprised between 50% and 80% of the conductive layer and the proportion of the silicone rubber to be in contact with the skin 12 is comprised between 20% and 50% in respect to the total conductive layer 2. In a most preferred embodiment the proportion of conductive layer 2 to be in contact with the skin 12 is comprised between 60% and 70% of the conductive layer 2 and the proportion of the silicone rubber to be in contact with the skin 12 is comprised between 30% and 40% in respect to the total conductive layer 2.

In a preferred embodiment the track 4 and the electric connector 5 are covered with an insulating material 8.

In sensor on contact with the skin of the user the electrode/skin resistance is one of the elements to determine the noise of the signals. In a preferred embodiment the resistance of the electrode 3 is comprised between 1Ω and 10Ω. In a more preferred embodiment the resistance of the track 4 is comprised between 1Ω and 50 kΩ.

A second aspect of the present invention is a device comprising at least one sensor 1 of the invention and an electronic instrument 14 for receiving and collecting and/or storing and/or processing, and/or transmitting data from said sensor.

Using the sensor of the invention, the physiological signals detected can be at least one of the following data: cardiac pulse, respiratory frequency, electrodermal response (EDR), measures electrical skin conductivity, electrocardiography (ECG), electromyography (EMG). These signals refer to electrical signals produced in the body. Preferably the data are ECG data.

A third aspect of the present invention is a garment 7 which integrates the device of the invention.

In an embodiment of the third aspect, the garment 7 is designed for applying a pressure equal or higher than 2 KPa. In another embodiment the garment 7 comprises two layers, an inner and an outer layer 13, and the outer layer 13 compresses the sensor to the body with at least 2 KPa. In a most preferred embodiment the outer layer 13 comprises a system to regulate the pressure.

Preferably, the inner layer has low elasticity and the outer layer 13 has high elasticity. The inner layer is comprised of a blend of synthetic fiber and spandex, wherein the synthetic fiber comprises 85% to 90% by weight of the composite elastic material and most preferably 87% to 89%, and wherein the spandex comprises 10% to 15% by weight of the composite elastic material, and most preferably 11% to 13%. The outer layer 13 is comprised of a blend of synthetic fiber and spandex, wherein the synthetic fiber comprises 92% to 97% by weight of the composite elastic material and most preferably 94% to 96%, and wherein the spandex comprises 3% to 8% by weight of the composite elastic material, and most preferably 4% to 6%. The outer layer 13 compresses the sensor to the skin, and the stability and fixation of the sensor 1 are improved.

In an embodiment of the third aspect, the track 4 of the conductive layer 2 of the sensor 1 is placed between the inner and the outer layer 13 of the garment, and the electrode 3 is over the inner layer of the garment, the electrode 3 being able to be in contact with the skin 12 of the user of the garment 7.

The sensor 1 can be prepared by a process comprising the steps of:
a) die cutting a conductive layer of conductive fabric;
b) adding a hot melt adhesive on one surface of the conductive layer;
c) screen printing with an anti-slip silicone rubber on the orifices 6 or grooves 11 of the electrode 3, at a temperature comprise between 10-30° C.; and
d) curing the silicone, preferably for up two minutes at a temperature comprised between 130-190° C.

The process can further comprise the step of screen printing with an silicone rubber loaded with an conductive material to form the track 4.

Figure 1B:
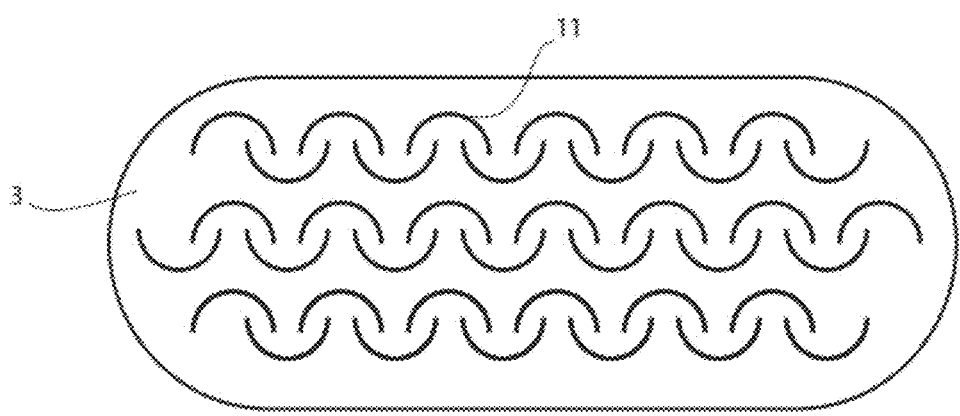
FIG. 1B illustrates an exemplary groove pattern in the electrode, in accordance with at least one embodiment.
Figure 1C:
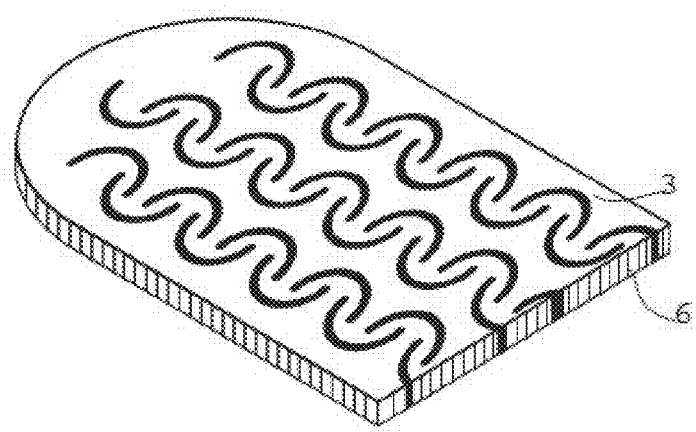
FIG. 1C illustrates an exemplary orifice pattern in the electrode with a silicone rubber pattern on the surface of the electrode, in accordance with at least one embodiment.
Figure 1D:
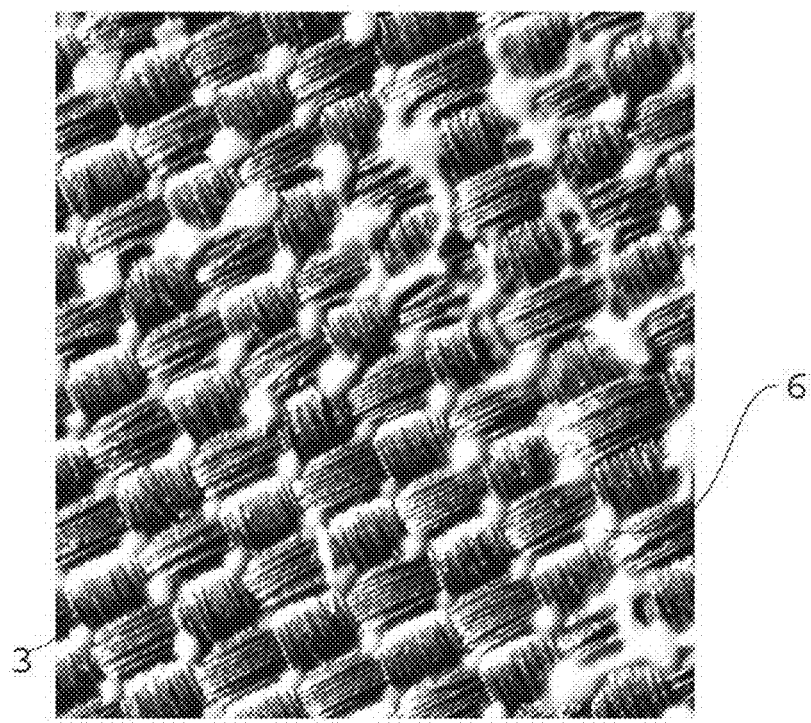
FIG. 1D illustrates a front view of a conductive fabric with the orifices filled with silicone rubber, in accordance with at least one embodiment.

A particular embodiment of the invention orifices 6 pattern of the electrode 3 is illustrated in FIG. 1A. FIG. 1B shows a preferred grooves pattern 11 of the electrode 3. FIG. 1C illustrates an electrode 3 with the orifices 6 filled with silicone rubber, wherein the electrode 3 shows the silicone rubber in a predefined pattern on their surface in a relief profile. Therefore, the silicone rubber anchorages with the fabric of the electrode, through the filling of the orifices.

Figure 2:
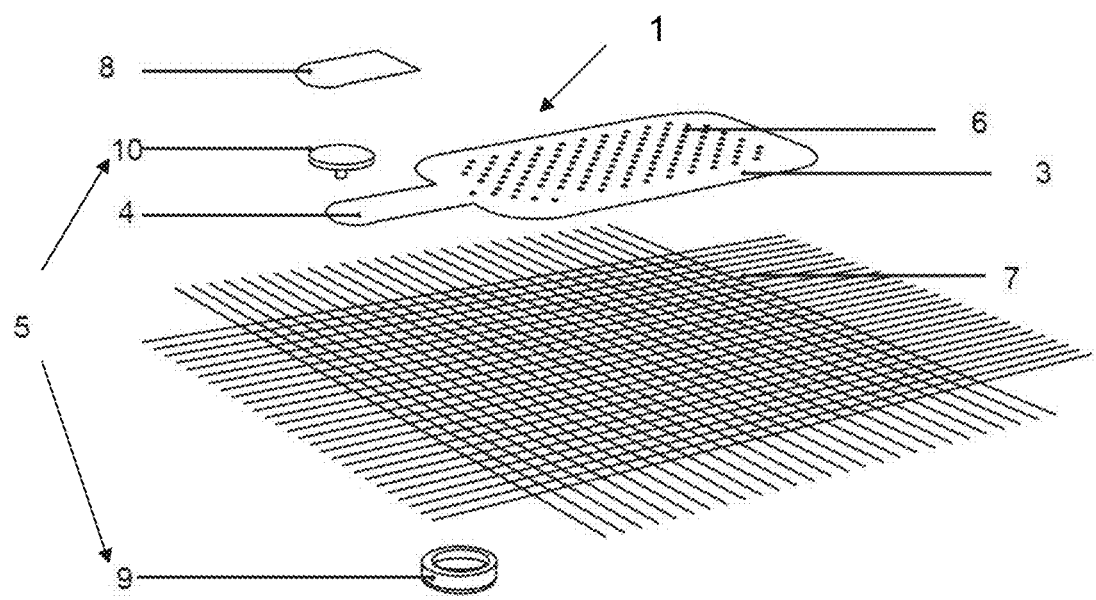
FIG. 2 illustrates an exploited perspective view of an embodiment of a sensor, in accordance with at least one embodiment.

FIG. 2 shows an exploited perspective view of a sensor 1 wherein the conductive layer 2 comprises the electrode 3 and track 4. As mentioned above, the electrode 3 present circular orifices 6 filled with silicone rubber. The electrical connector 5 is in contact with the track 4 of the conductive layer 2 and the track 4 can be covered with an insulating material 8. The electrical connector 5 comprises a first and second portion, wherein the first portion comprise a female-type clip portion 9 and the connector second portion may comprise a male-type stud portion 10, which portions mate with each other.

Alternatively, the connector first portion may comprise a male-type stud portion and the connector second portion may comprise a female-type clip portion, which portions mate with each other. Typically, when the sensor 1 is integrated in a garment 7, male a female portions of the electrical connector are placed on the opposite face of the garment each other. Thus, the male or female portion which is placed in the inner face, which will be in contact with the skin 12 of the user, is covered with an insulating material 8, which also covers the track 4 of the conductive layer 2.

Figure 3A:
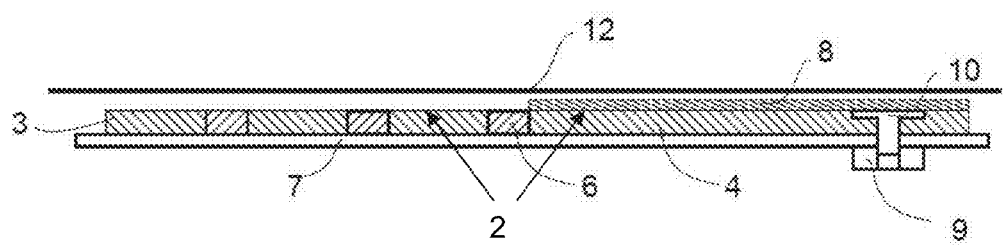
FIG. 3A illustrates a cross-section of an embodiment of a sensor, in accordance with at least one embodiment.

FIG. 3A illustrates a cross-section of the sensor 1 of the invention. The cross-section of the sensor 1 shows the electrode area 3 and the circular orifices 6 filled with silicone rubber. The track 4 is made of the same material than the electrode 3. The track and the electrode are made of conductive fabric. The sensor of the invention is in contact with the skin 12.

Figure 3B:
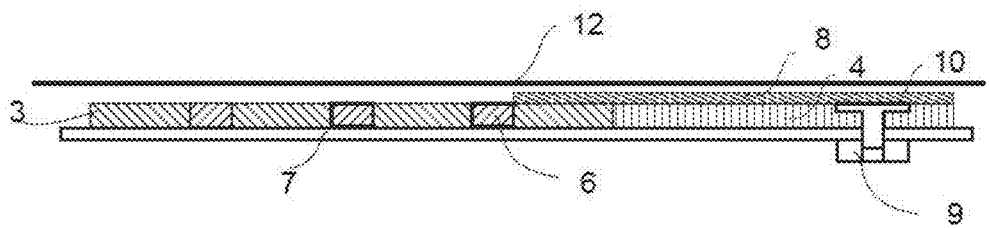
FIG. 3B illustrates a cross-section of an embodiment of a sensor, in accordance with at least one embodiment.

FIG. 3B illustrates a cross-section of an embodiment of a sensor 1 according to the present invention. In this embodiment the electrode is made of conductive fabric and the track 4 is made of silicone rubber loaded with a conductive material.

Figure 4:
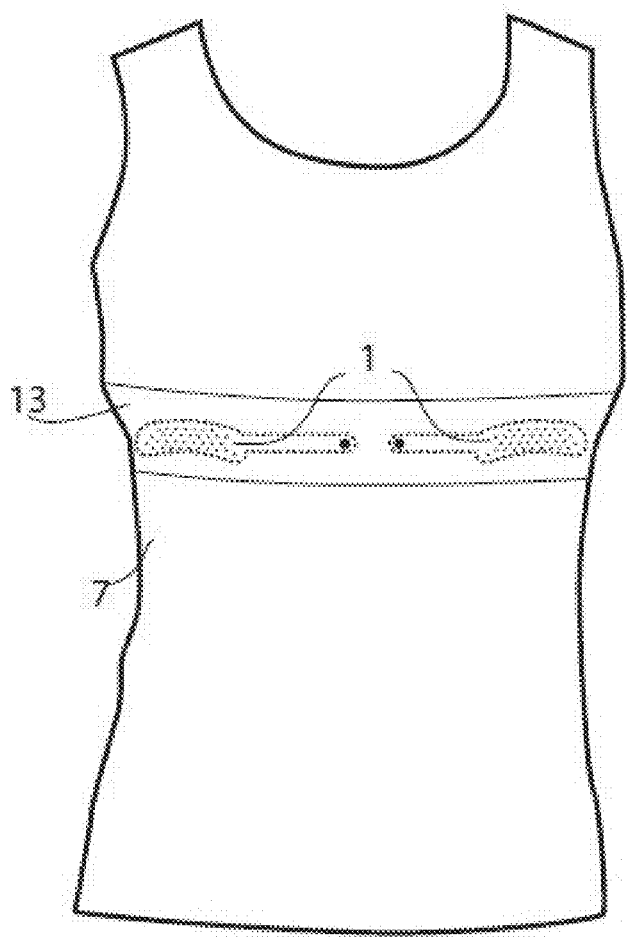
FIG. 4 illustrates an elevation view of the garment, in accordance with at least one embodiment.

FIG. 4 illustrates an elevation view of the garment 7 with two sensor 1 placed near the chest area. The outer layer 13 of the garment 7 presses the sensor with at least 2 KPa.

Figure 5:
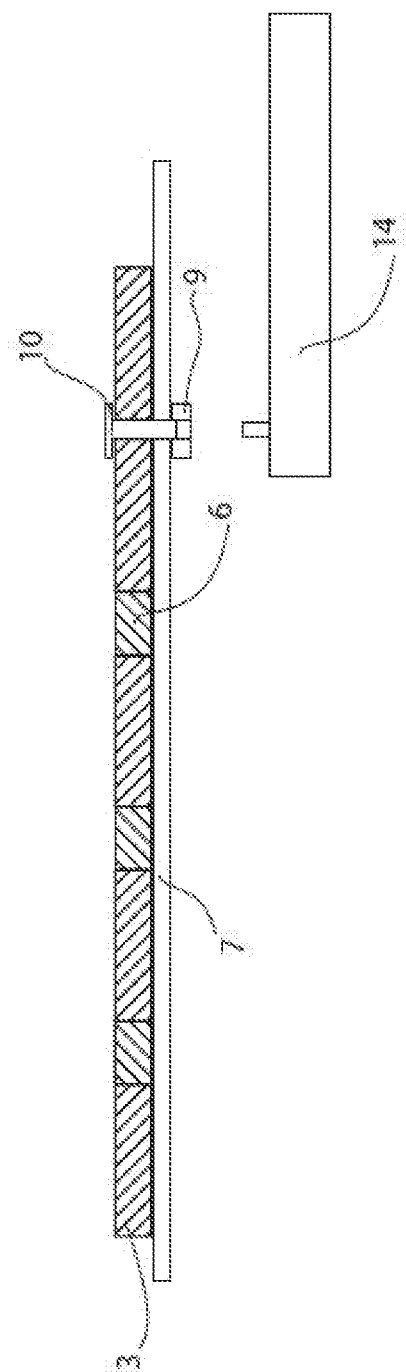
FIG. 5 illustrates a cross-section elevation view of a connection between an embodiment of a sensor and an electronic instrument, in accordance with at least one embodiment.

FIG. 5 illustrates a cross-section elevation view of a connection between an embodiment of a sensor 1 according to the present invention and an electronic instrument 14. The sensor 1 is connected to the electronical connector 5 using a female-type clip portion 9 and a male-type stud portion 10.

Throughout the description and claims the word "comprise" and variations of the word, are not intended to exclude other technical features, additives, components, or steps. Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim, and shall not be construed as limiting the scope of the claim. Furthermore, the present invention covers all possible combinations of particular and preferred embodiments described herein.

Comparative Example Between a Garment with the Sensor of the Invention and Other Garments with Fabric Sensor Technology Zephyr™ HxM (made by Zephyr Technology Corporation) (I), Polar TEAM$^2$ (made by Polar Electro, OY.) (II), Numetrex® Cardio-Shirt (made by Textronics, Inc.) (Ill) and the shirt of the invention (IV), wherein the track and the electrode are made of conductive fabric and the electrode area has the orifices filled with silicone rubber, were tried. The Numetrex® Cardio-Shirt is a shirt with textile electrodes knitted into the fabric. The Zephyr™ HxM strap and Polar TEAM$^2$ strap are straps with textile electrodes. The Zephyr™ HxM strap includes an electrode and a resilient compressible filler provided between the garment and the electrode such that, in use, the electrode is held substantially in place against the skin when the garment moves relative to the user's skin. The Polar TEAM$^2$ strap includes a contact layer including conductive fibres, and a moisture layer for retaining moisture on top of the contact layer.

The test protocol in which performed activities were divided in different levels of physical exigency: resting, daily activity and strong physical activity.

The subject was monitored with a device compatible with all the straps and shirts tested.

The exercises of the protocol were defined as following:
Resting (A): the subject remained lay down in a table for 30 seconds.
Daily activity is defined by:
Stand (B): the subject stood on his feet still for 20 seconds without moving.
Sit down/stand up (C): the subject sat down and stood up of a chair 4 times, remaining 3 seconds in each state.
Bend down (D): the subject bent down 3 times, always in the same way (without flexing his knees).
Arm movement (E): the subject moved his arms in different directions (straight, horizontal and vertical) 3 times each.
Walk (F): The subject walked at a approximate speed of 3 km/h for 20 seconds.

Strong Physical Activity (H) is Defined by

Moderate-speed Running (I): the subject ran at a speed of 6 km/h during 20 seconds.
Fast-speed Running (J): the subject sped up his pace until he reached 10 km/h, then he stayed running at this speed during 15 seconds.
Strong arm movement (racket move) (K): the subject moved his arm strongly simulating hitting a ball with a racket (with both arms), doing this movement 5 times.
Torso turning (L): keeping the feet in the same position, the subject turned his torso in both directions, 5 times each.
Jumping (M): the subject jumped high, he will run two or three meters and then he will jumped again. He repeated this movement 5 times.

Strong physical activity, were more physical demanding than the daily activity. It is also important to underline that the subject sweated during these exercises, so all of the results were in these conditions.

All the exercises done in the resting and daily activities were with the strap or shift put directly onto the subject (no sweat) and all the strong physical activity was done with the strap or shirt worn by the subject when he was already sweat.

When the different electrocardiographic signals were obtained with each shirt or strap were performed a sort of measures over these signals to evaluate the different technologies.

The measures performed on the signals were (for each exercise of each activity):

Visual Measures

This measure is a direct recognition, just by watching the signal, of the quality of the signal acquired in terms of morphology and beats detected. This visual recognition is also used to identify what beats (QRS complexes) are recognizable as beats and which of them are too noisy to be recognized by a cardiologist. A total of 250 beats were analyzed for resting and Daily Activity and for Strong Physical Activity. A total of 500 beats were analyzed.

Measures Over the Signal

These measures were made on the signal registered in each exercise of each activity session. These measures involve manual and automatic analysis of the recorded signals.

Autocorrelation:

The signal was segmented each 3 seconds with an overlap of 2 seconds between blocks and the autocorrelation was done of each block. This measure follows the next formula:

$$R_x(m) = (1/N - |m|) \sum_{n=0}^{N-1} x_n x_{n+m}$$

where x is a signal of N samples. Then it's normalized regarding to the value of $R_x$ (0). Then we obtain the autocorrelation maximum that it's not the one in $R_{x\,norm}$ (0), because it's sure that we have a maximum in this point because the signal is compared with itself without shift.

This index give us a measure of how much does the signal resemble to a shifted itself (starting from the premise that a heartbeat and the next one are very similar). In this way, values close to 1 show that the signal is very similar to a shifted copy of itself, so it's clean of noise, while low values closet o zero show that the signal is corrupted by noise.

T-P Segment RMS:

The RMS (Root Mean Square) of the T-P segment was calculated in between heartbeats (aprox. 20 segments). This measure was done for each exercise and, averaged, give an estimate of the noise in the signal, particularly in Resting state, because the T-P segment is isoelectric.

These measures were done manually (to select the beginning and end of each segment). In those signals where the T wave was not present (Zephyr™ HxM and Polar TEAM² straps and Numetrex® Cardio-Shirt in Resting and Daily Activity), the segment is defined between two consecutive heartbeats. This value has to be as low as possible but has to be contextualized with the QRS amplitude (see the point RMS/AmplitudeRS).

Maximum T-P Segment:

It measures the maximum peak of noise of the different T-P segments. This value was useful to see if high peaks of noise contaminate our signal.

Maximum Amplitudes:

The amplitudes of the QRS peaks was measured (R peaks and S peaks, to get RS amplitude) for the beats of each exercise. There was not a preferred value but higher values tend to be better to low ones (low ones are more prone to noise).

RMS/AmplitudeRS:

This factor was calculated with the measures explained in the previous points. This index gives us and accurate idea of the noise of the system in the different exercises. It's normalized regarding to the RS Amplitude because each shirt/strap captures a different amount of signals, different amplitudes, so RMS in the T-P segment has to be contextualized to each sensor strap or shirt. For this value, the lower the better.

Of all the index and values obtained, the most important ones are RMS/AmplitudeRS and Autocorrelation because both of them are very good indicators of the noise that contaminate the signals and how recognizable are the heartbeats in the registered signals.

The results were presented divided in three sections: results for Resting and Daily Activity, results for Strong Physical Activity.

Resting and Daily Activity

Figure 6:
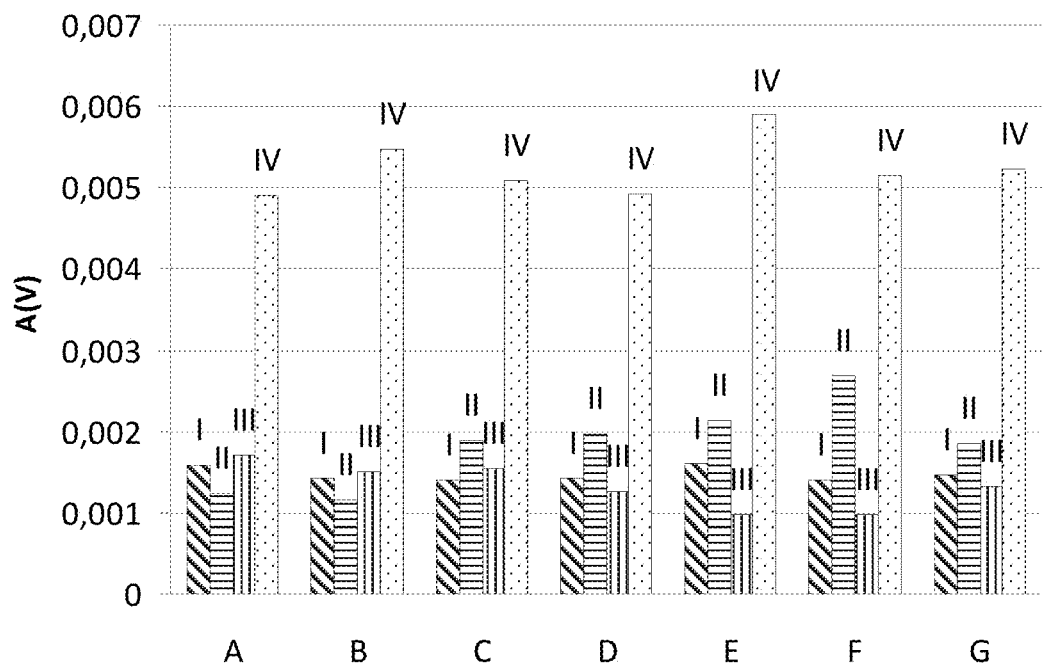
FIG. 6 shows the Amplitude RS (A(v)) in resting (A), stand (B), stand/sit (C), bend (D), arms (E), walk (F), and all the activities, resting, stand stand/sit, bend arms and walk (G) for Zephyr™ HxM strap (I), Polar TEAM$^2$ strap (II), Numetrex® Cardio-Shirt (III) and the shirt of the invention (IV), in accordance with at least one embodiment.

FIG. 6 shows the amplitude RS (A(v)) in resting (A), stand (B), stand/sit (C), bend (D), arms (E), walk (F), and all the activities, resting, stand stand/sit, bend arms and walk (G) for Zephyr™ HxM strap (I), Polar TEAM² strap (II), Numetrex® Cardio-Shirt (III) and the shirt of the invention (IV). The amplitude RS gives an idea of how much signal does our system capture, so a high amplitude RS is better. FIG. 6 shows that the shirt of the invention captures better signal than the other systems, it works better in dry conditions (this activity session doesn't involves sweating).

Figure 7:
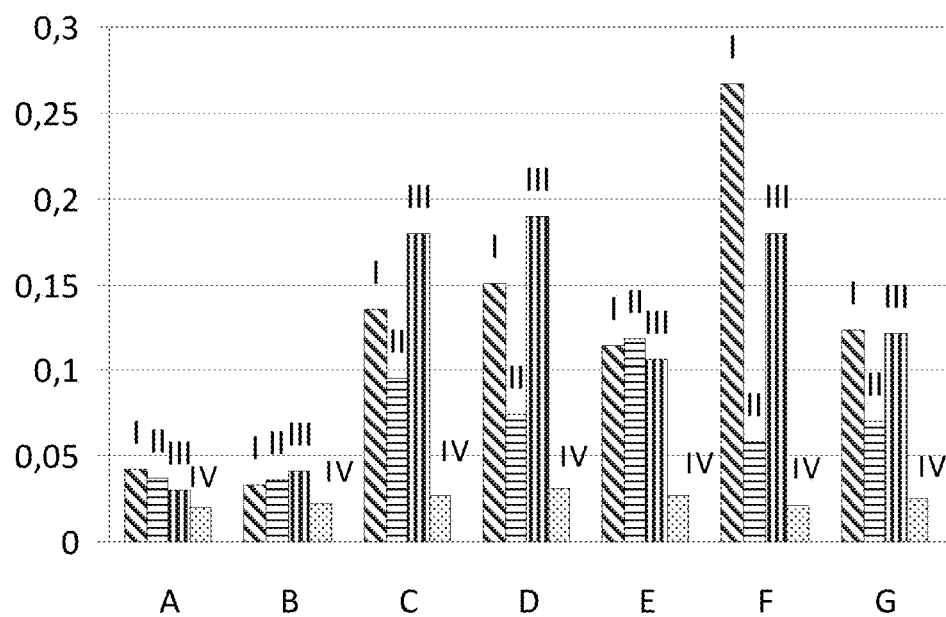
FIG. 7 shows RMS/Amplitude RS in resting (A), stand (B), stand/sit (C), bend (D), arms (E), walk (F), and all the activities, resting, stand stand/sit, bend arms and walk (G) for Zephyr™ HxM strap (I), Polar TEAM$^2$ strap (II), Numetrex® Cardio-Shirt (III) and the shirt of the invention (IV), in accordance with at least one embodiment.

FIG. 7 shows RMS/Amplitude RS in resting (A), stand (B), stand/sit (C), bend (D), arms (E), walk (F), and resting and daily activity (resting, stand stand/sit, bend arms and walk) (G) for Zephyr™ HxM strap (I), Polar TEAM² strap (II), Numetrex® Cardio-Shirt (III) and the shirt of the invention (IV). This data is important because the noise is contextualized regarding to the AmplitudeRS, and it's a good measure of the SNR (Signal-to-Noise Ratio) of the system. The value calculated here is Noise-to-Signal, so the lower this value is the better. The shirt of the invention (IV) show the lowest value.

Figure 8:
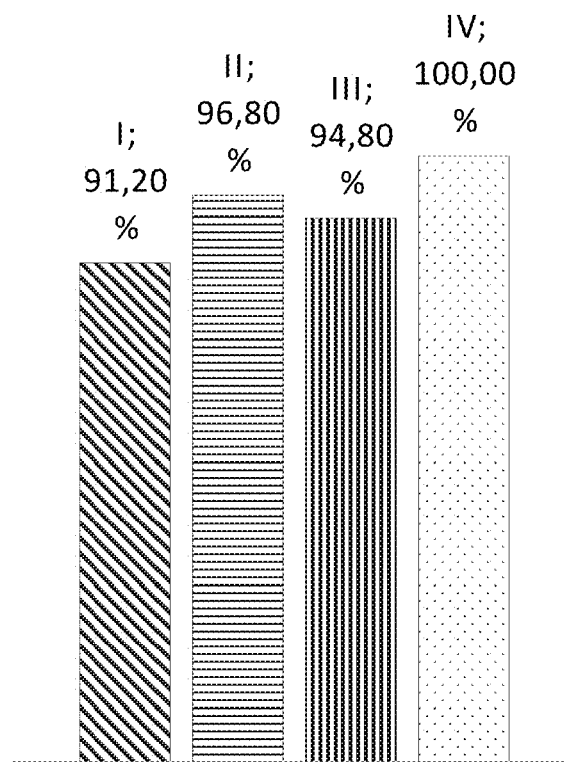
FIG. 8 shows the percentage of good QRS complex in resting and daily activity for Zephyr strap (I), Polar strap (II), Numetrex shirt (III) and the shirt of the invention (IV), in accordance with at least one embodiment.

FIG. 8 shows the percentage good QRS complex in resting and daily activity for Zephyr™ HxM strap (I), Polar TEAM² strap (II), Numetrex® Cardio-Shirt (III) and the shirt of the invention (IV). FIG. 8 determines how many beats are recognizable as QRS at first sight. A total of 250 beats were analyzed for each system, and the results here are the total of the Resting and Daily Activity Session (not divided into exercises). The higher the percentage is the better. The highest value it is the value of the shirt of the invention (IV).

Figure 9:
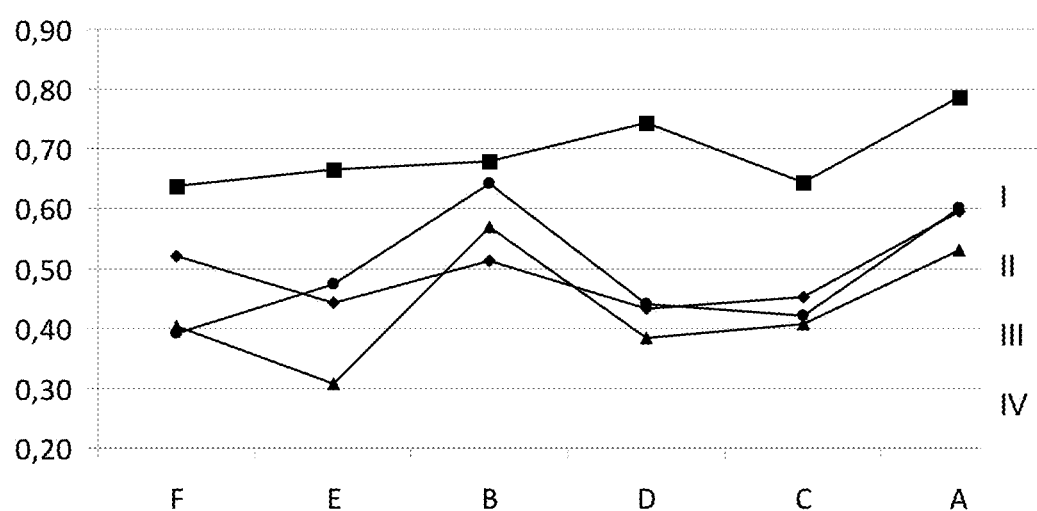
FIG. 9 shows the autocorrelation value for Zephyr™ HxM strap (I), Polar TEAM$^2$ strap (II), Numetrex® Cardio-Shirt (III) and the shirt of the invention (IV), in walking (F), arms (E), stand (B), bend (D), stand/sit (C) and resting (A), in accordance with at least one embodiment.

FIG. 9 shows the autocorrelation value for Zephyr™ HxM strap (I), Polar TEAM² strap (II), Numetrex® Cardio-Shirt (III) and the shirt of the invention (IV) in walking (F), arms (E), stand (B), bend (D), stand/sit (C) and resting (A). This information is also important because it is a good indicator of the quality, reproducibility and the similitude between the heartbeats. The closer this value is to 1, the better. The shirt of the invention show the closest value to 1.

Strong Physical Activity

Figure 10:
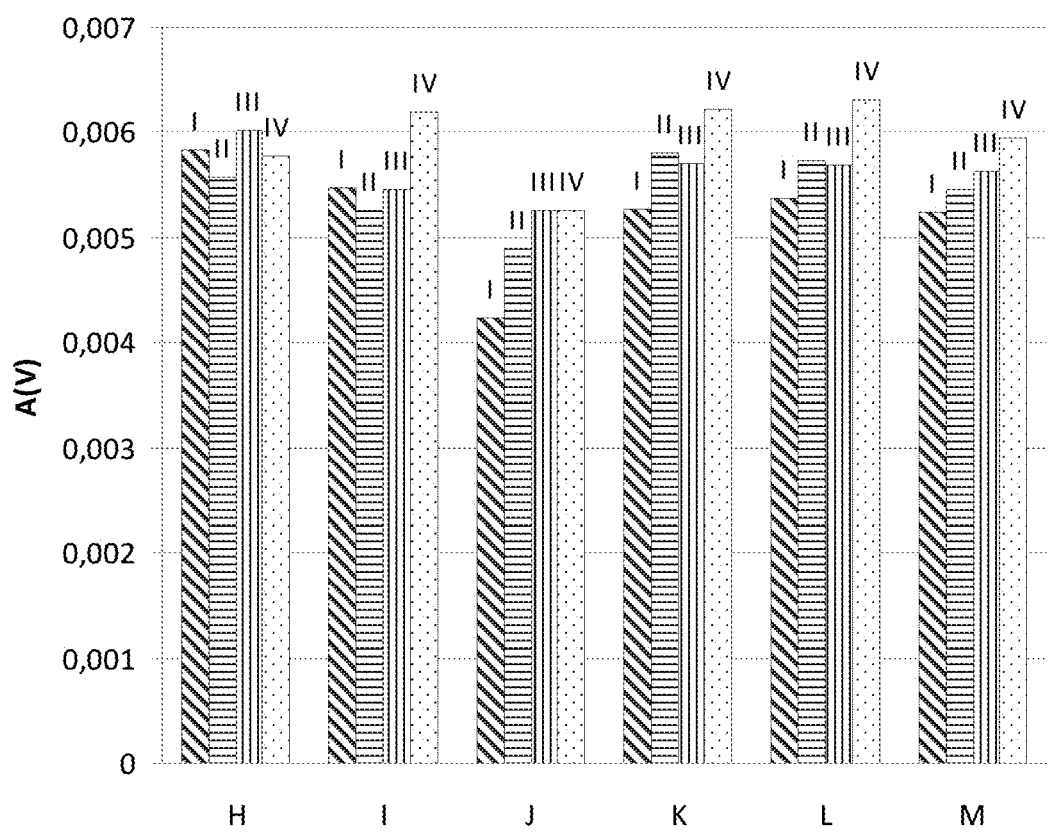
FIG. 10 shows the Amplitude RS (A(v)) in mid-speed (H), fast-speed (I), torso-move (J), racket (K), jump (L), and all the activities, mid-speed, fast-speed, torso move, racket and jump (M) for Zephyr™ HxM strap (I), Polar TEAM$^2$ strap (II), Numetrex® Cardio-Shirt (III) and the shirt of the invention (IV), in accordance with at least one embodiment.

FIG. 10 shows the Amplitude RS (A(v)) in mid-speed (H), fast-speed (I), torso-move (J), racket (K), jump (L), and all the activities, (mid-speed, fast-speed, torso move, racket and jump) (M) Zephyr™ HxM strap (I), Polar TEAM$^2$ strap (II), Numetrex® Cardio-Shirt (III) and the shirt of the invention (IV). In Strong Physical Activity, due to the sweat, the amplitude of the signal is more similar between technologies, because the sweat helps the conduction of the electric potentials to the electrode and decreases the impedance of the skin-electrode interface.

Figure 11:
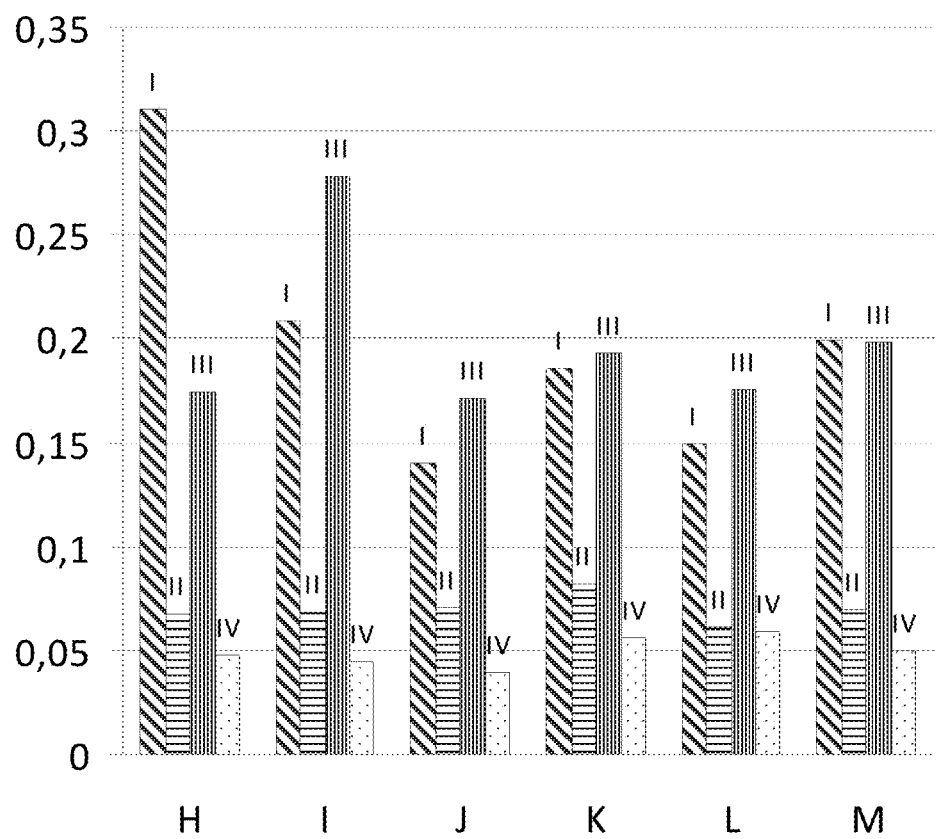
FIG. 11 shows RMS/Amplitude RS in mid-speed (H), fast-speed (I), torso-move (J), racket (K), jump (L), and all the activities, mid-speed, fast-speed, torso move, racket and jump (M) for Zephyr strap (I), Polar strap (II), Numetrex shirt (III) and the shirt of the invention (IV), in accordance with at least one embodiment.

FIG. 11 shows RMS/Amplitude RS in mid-speed (H), fast-speed (I), torso-move (J), racket (K), jump (L), and all the activities, mid-speed, fast-speed, torso move, racket and jump (M) for Zephyr™ HxM strap (I), Polar TEAM$^2$ strap (II), Numetrex® Cardio-Shirt (III) and the shirt of the invention (IV). Again, we can see here that the shirt of the invention has the best results.

Figure 12:
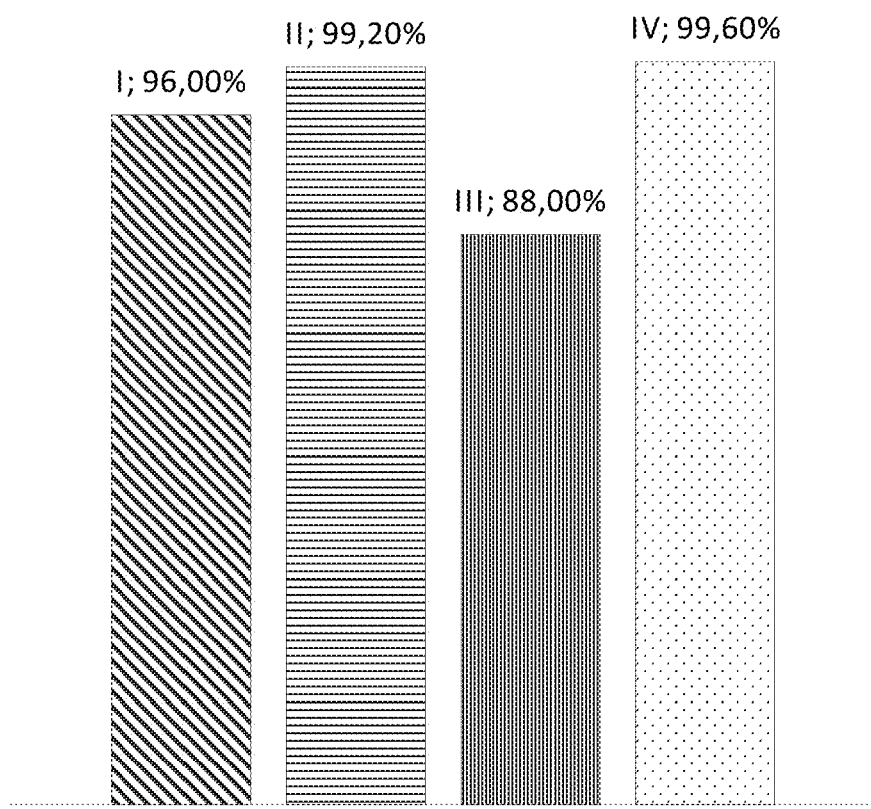
FIG. 12 shows the percentage of good QRS complex in strong physical activity for Zephyr strap (I), Polar strap (II), Numetrex shirt (III) and the shirt of the invention (IV), in accordance with at least one embodiment.

FIG. 12 shows the percentage good QRS complex in strong physical activity for Zephyr™ HxM strap (I), Polar TEAM$^2$ strap (II), Numetrex® Cardio-Shirt (III) and the shirt of the invention (IV). The shirt of the invention shows the best results.

Figure 13:
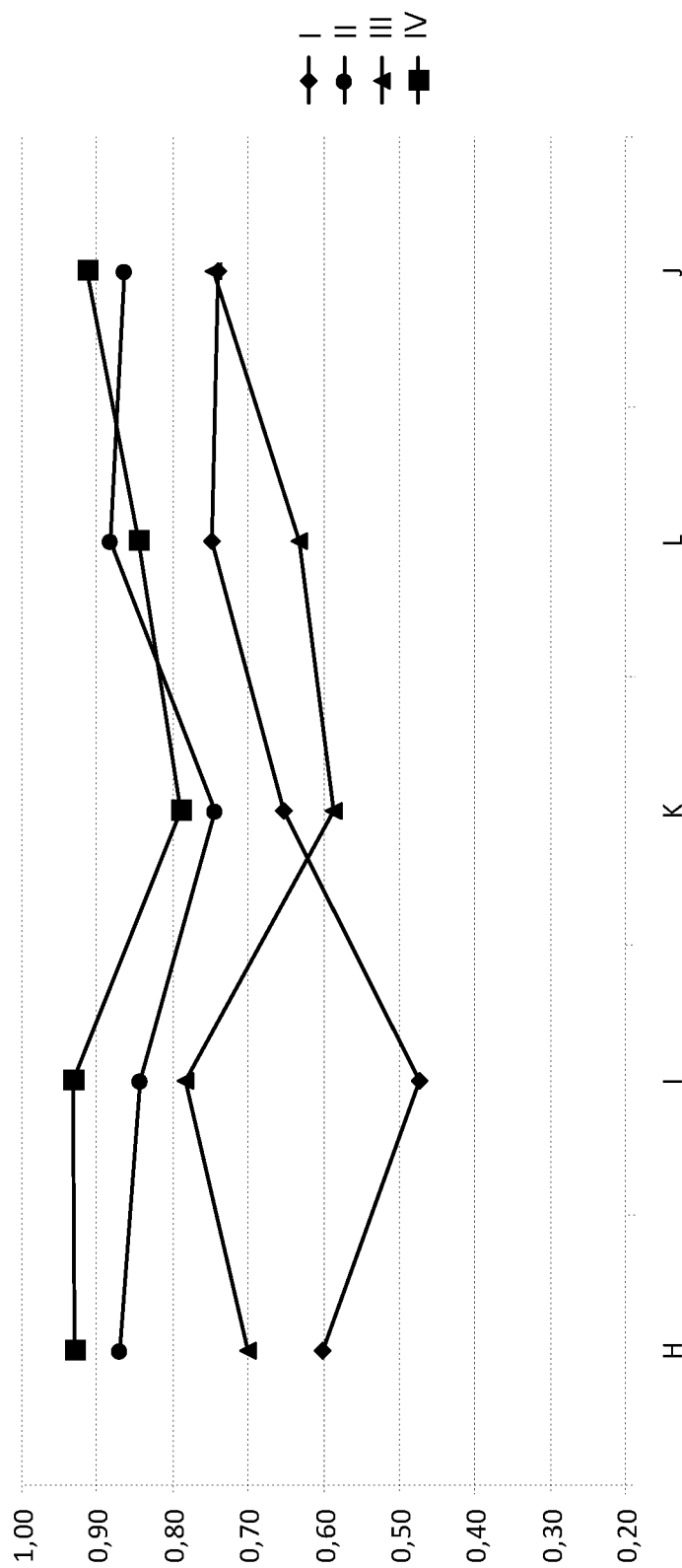
FIG. 13 shows the autocorrelation value Zephyr™ HxM strap (I), Polar TEAM$^2$ strap (II), Numetrex® Cardio-Shirt (III) and the shirt of the invention (IV) in mid-speed (H), fast-speed (I), torso-move (J), racket (K) and jump (L), in accordance with at least one embodiment.

FIG. 13 shows the autocorrelation value for Zephyr™ HxM strap (I), Polar TEAM$^2$ strap (II), Numetrex® Cardio-Shirt (III) and the shirt of the invention (IV) in mid-speed (H), fast-speed (I), torso-move (J), racket (K) and jump (L). The shirt of the invention shows the best result.

In conclusion the shirt of the invention seems superior when we are in a situation of dry interface skin-electrode (no sweating), giving a much better signal and more stable than the other systems. In a Strong Physical situations, all the systems work better in terms of signal capture thanks to the sweat, but the shirt of the invention is the one that give a more signal recognizable morphology and stable signal and gives the best result in all of the situations and activities.

Comparative Example Between a Garment with the Sensor of the Invention and the Garments with the Sensor of the Invention where the Orifices of the Electrode Area were not Filled with Silicone Rubber.

The shirt of the invention (IV), wherein the track and the electrode are made of conductive fabric and the electrode area has the orifices filled with silicone rubber, and the shirt of the invention without silicone rubber (V) were tried.

The protocol followed was the same described above. Significant differences were obtained in strong physical activity.

Figure 14:
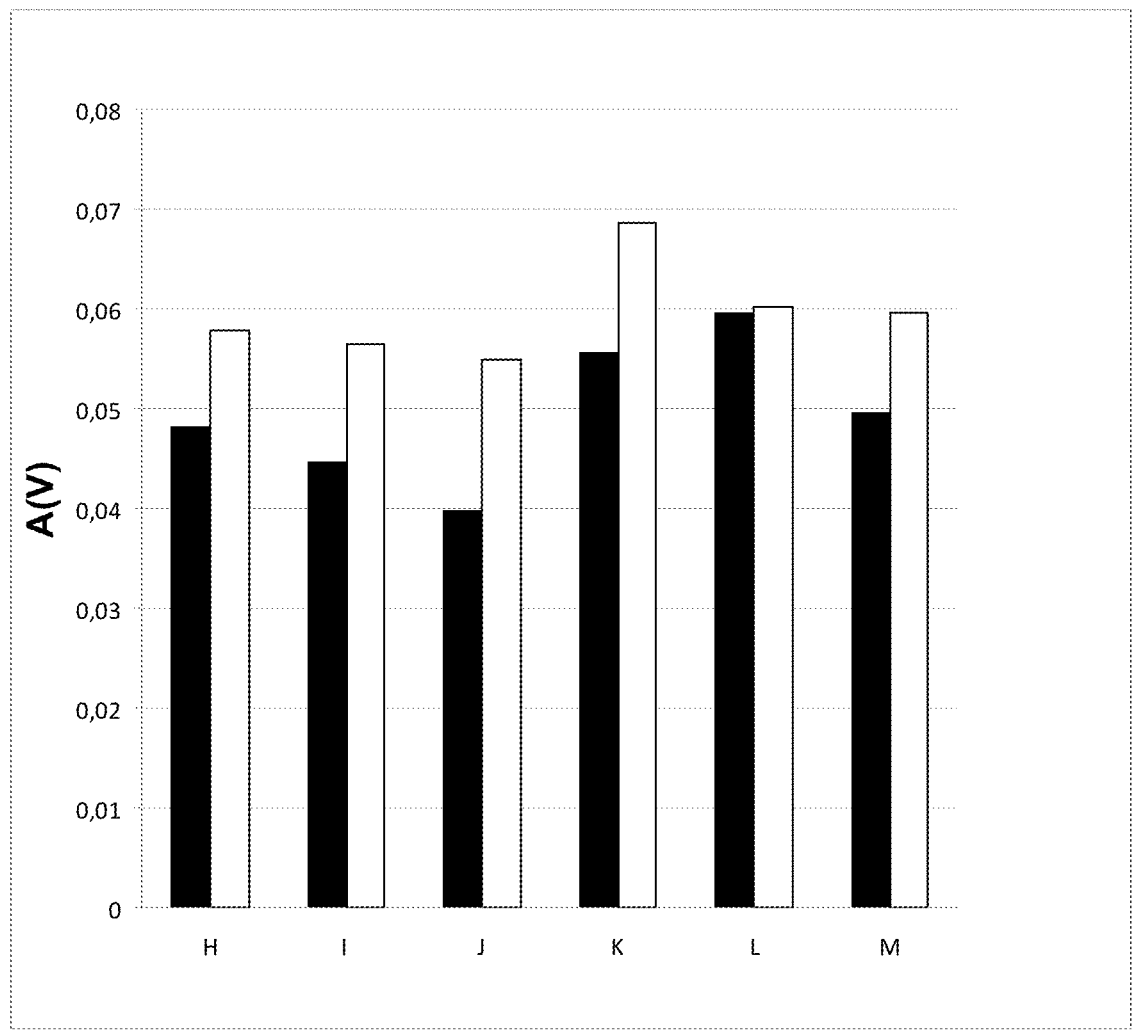
FIG. 14 shows RMS/Amplitude RS in mid-speed (H), fast-speed (I), torso-move (J), racket (K), jump (L), and all the activities, mid-speed, fast-speed, torso move, racket and jump (M) for the shirt of the invention (IV), black column and the shirt of the invention without silicone rubber (V), white column, in accordance with at least one embodiment.

FIG. 14 shows RMS/Amplitude RS in mid-speed (H), fast-speed (I), torso-move (J), racket (K), jump (L), and all the activities, mid-speed, fast-speed, torso move, racket and jump (M) for the shirt of the invention (IV) and the shirt of the invention without silicone rubber. The shirt of the invention has the best results, this means less noise and better signal with silicone than without it. The results showed the better adherence to the skin.

Aspects of the present specification may also be described as follows:

1. A device comprising: an at least one sensor for acquiring physiological signals, the at least one sensor comprising: a conductive layer comprising a conductive fabric of interlaced conductive and non-conductive fibers and a plurality of orifices throughout the conductive fabric, wherein the plurality of orifices are filled with a silicone rubber, and wherein the silicone rubber is attached to the conductive fabric without the use of an adhesive; and an electrical connector connected to the conductive layer, the electrical connector providing a separable interface between the conductive layer and an electronic instrument; and an electronic instrument for receiving and collecting signals acquired from the at least one sensor.

2. The device according to embodiment 1, wherein the conductive layer of the at least one sensor comprises at least an electrode and a track, the electrical connector being connected to the track.

3. The device according to embodiments 1-2, wherein the track of the at least one sensor is covered with an insulating material.

4. The device according to embodiments 1-3, wherein the conductive fibers of the at least one sensor comprise 1) fibers including silver, copper, nickel, stainless steel, gold, silicone rubber loaded with carbon or silver powder; 2) non-conductive fibers coated with a conductive material; or 3) a mixture thereof.

5. The device according to embodiments 1-4, wherein the non-conductive fibers of the at least one sensor comprise fibers including wool, silk, cotton, flax, jute, acrylic, polyamide polyester, nylon, or elastic yarn.

6. The device according to embodiments 1-5, wherein the conductive fibers of the at least one sensor comprise fibers made of silver coated nylon and the non-conductive fibers are made of nylon.

7. The device according to embodiments 1-6, wherein the silicone rubber of the at least one sensor is a silicone rubber with molecular weight comprised between 400 g/mol and 600 g/mol.

8. The device according to embodiments 1-7, wherein the proportion of the conductive layer of the at least one sensor designed to be in contact with a skin surface comprises between 50% and 80% of the conductive layer and the proportion of the silicone rubber designed to be in contact with the skin surface comprises between 20% and 50% of the conductive layer.

9. The device according to embodiments 1-8, wherein the electronic instrument further stores and/or processes and/or transmits data received and collected from the at least one sensor.

10. The device according to embodiments 1-9, wherein the at least one sensor is coupled to the garment so as to be placed in contact with skin of a user during the use of the garment.

11. The device according to embodiments 1-10, wherein a portion of the garment which is coupled to the sensor is designed for applying a pressure equal or higher than 2 kPa.

12. The device according to embodiments 1-11, wherein the garment comprises two layers comprising an inner and an outer layer, and the outer layer is able to compress the sensor to a body of the user with a pressure of at least 2 kPa.

13. The device according to embodiments 1-12, wherein the outer layer comprises a system to regulate the pressure.

14. A process for the preparation of an at least one sensor as defined in embodiments 1-13, the process comprising the steps of: a) die cutting the conductive fabric; b) adding a liquid silicone in a manner that the liquid silicone penetrates and fills the plurality of orifices present in the conductive fabric; and c) curing the liquid silicone to form the silicone rubber; wherein steps a) and b) can be carried out in any order.

15. The device according to embodiments 1-13, wherein the plurality of orifices of the at least one sensor form an organized pattern.

16. The device according to embodiments 1-13 and 15, wherein the organized pattern is a circular pattern, sinusoidal pattern, straight line pattern, hexagon pattern, another pattern of geometric shapes, or a combination thereof.

17. The device according to embodiments 1-13 and 15-16, wherein the silicone rubber of the at least one sensor is located only in the plurality of orifices.

18. The device according to embodiments 1-13 and 15-17, wherein the at least one sensor is configured for detecting cardiac pulse, respiratory frequency, electrodermal response, electrical skin conductivity, electrocardiography, and/or electromyography.

In closing, regarding the exemplary embodiments of the present invention as shown and described herein, it will be appreciated that sensors and associated devices are disclosed and configured for acquiring physiological signals. Because the principles of the invention may be practiced in a number of configurations beyond those shown and described, it is to be understood that the invention is not in any way limited by the exemplary embodiments, but is generally directed to sensors and associated devices and is able to take numerous forms to do so without departing from the spirit and scope of the invention. It will also be appreciated by those skilled in the art that the present invention is not limited to the particular geometries and materials of construction disclosed, but may instead entail other functionally comparable structures or materials, now known or later developed, without departing from the spirit and scope of the invention.

Certain embodiments of the present invention are described herein, including the best mode known to the inventor(s) for carrying out the invention. Of course, variations on these described embodiments will become apparent to those of ordinary skill in the art upon reading the foregoing description. The inventor(s) expect skilled artisans to employ such variations as appropriate, and the inventor(s) intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (along with equivalent open-ended transitional phrases thereof such as "including," "containing" and "having") encompasses all the expressly recited elements, limitations, steps and/or features alone or in combination with un-recited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amendment for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim, whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (along with equivalent open-ended transitional phrases thereof) includes within its meaning, as a limiting case, claimed subject matter specified by the closed-ended transitional phrases "consisting of" or "consisting essentially of." As such, embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

While aspects of the invention have been described with reference to at least one exemplary embodiment, it is to be clearly understood by those skilled in the art that the invention is not limited thereto. Rather, the scope of the invention is to be interpreted only in conjunction with the appended claims and it is made clear, here, that the inventor(s) believe that the claimed subject matter is the invention.

What is claimed is:

1. A device comprising:
    an at least one sensor for acquiring physiological signals and an electronic instrument for receiving and collecting signals acquired from the at least one sensor; and
    the at least one sensor comprising:
        a conductive layer comprising:
            a conductive fabric of interlaced conductive and non-conductive fibers and a plurality of orifices throughout the conductive fabric, wherein the plurality of orifices are filled with a silicone rubber, and wherein the silicone rubber is attached to the conductive fabric without the use of an adhesive;
        an electrode; and
        a track; and
    an electrical connector connected to the track of the conductive layer, the electrical connector providing a separable interface between the conductive layer and the electronic instrument.

2. The device of claim 1, wherein the track of the at least one sensor is covered with an insulating material.

3. The device of claim 1, wherein the conductive fibers of the at least one sensor comprise 1) fibers including silver, copper, nickel, stainless steel, gold, silicone rubber loaded with carbon or silver powder; 2) non-conductive fibers coated with a conductive material; or 3) a mixture thereof.

4. The device of claim 1, wherein the non-conductive fibers of the at least one sensor comprise fibers including wool, silk, cotton, flax, jute, acrylic, polyamide polyester, nylon, or elastic yarn.

5. The device of claim 1, wherein the conductive fibers of the at least one sensor comprise fibers made of silver coated nylon and the non-conductive fibers are made of nylon.

6. The device of claim 1, wherein the silicone rubber of the at least one sensor is a silicone rubber with molecular weight comprised between 400 g/mol and 600 g/mol.

7. The device of claim 1, wherein the proportion of the conductive layer of the at least one sensor designed to be in contact with a skin surface comprises between 50% and 80% of the conductive layer and the proportion of the silicone rubber designed to be in contact with the skin surface comprises between 20% and 50% of the conductive layer.

8. The device of claim 1, wherein the electronic instrument further stores and/or processes and/or transmits the signals received and collected from the at least one sensor.

9. A garment comprising the device as defined in claim 1, wherein the at least one sensor is coupled to the garment so as to be placed in contact with skin of a user during the use of the garment.

10. The garment of claim 9, wherein a portion of the garment which is coupled to the sensor is designed for applying a pressure equal or higher than 2 kPa.

11. The garment of claim 9, wherein the garment comprises two layers comprising an inner and an outer layer, and the outer layer is able to compress the sensor to a body of the user with a pressure of at least 2 kPa.

12. The garment of claim 11, wherein the outer layer comprises a system to regulate the pressure.

13. The device of claim 1, wherein the plurality of orifices of the at least one sensor form an organized pattern.

14. The device of claim 13, wherein the organized pattern is a circular pattern, sinusoidal pattern, straight line pattern, hexagon pattern, another pattern of geometric shapes, or a combination thereof.

15. The device of claim 1, wherein the silicone rubber of the at least one sensor is located only in the plurality of orifices.

16. The device of claim 1, wherein the at least one sensor is configured for detecting cardiac pulse, respiratory frequency, electrodermal response, electrical skin conductivity, electrocardiography, and/or electromyography.

17. A process for the preparation of an at least one sensor as defined in claim 1, the process comprising the steps of:
    a) die cutting the conductive fabric;
    b) adding a liquid silicone in a manner that the liquid silicone penetrates and fills the plurality of orifices present in the conductive fabric; and
    c) curing the liquid silicone to form the silicone rubber; wherein steps a) and b) can be carried out in any order.

* * * * *